(12) United States Patent
Nemoto (10) Patent No.: US 9,918,687 B2
(45) Date of Patent: Mar. 20, 2018

(54) X-RAY CT SYSTEM, CHEMICAL LIQUID INJECTOR, AND CT SCANNER

(75) Inventor: Shigeru Nemoto, Tokyo (JP)

(73) Assignee: NEMOTO KYORINDO CO., LTD., Bunkyo-ku, Tokyo (JP)

(*) Notice: Subject to any disclaimer, the term of this patent is extended or adjusted under 35 U.S.C. 154(b) by 414 days.

(21) Appl. No.: 12/376,955

(22) PCT Filed: Aug. 3, 2007

(86) PCT No.: PCT/JP2007/065269
§ 371 (c)(1),
(2), (4) Date: Feb. 26, 2009

(87) PCT Pub. No.: WO2008/018385
PCT Pub. Date: Feb. 14, 2008

(65) Prior Publication Data
US 2010/0189210 A1 Jul. 29, 2010

(30) Foreign Application Priority Data
Aug. 7, 2006 (JP) .................................. 2006-214697

(51) Int. Cl.
*A61B 6/03* (2006.01)
*A61B 6/00* (2006.01)
(Continued)

(52) U.S. Cl.
CPC .............. *A61B 6/504* (2013.01); *A61B 6/465* (2013.01); *A61B 6/467* (2013.01); *A61M 5/007* (2013.01);
(Continued)

(58) Field of Classification Search
CPC ......... A61B 6/465; A61B 6/504; A61B 6/467; A61M 2205/502; A61M 5/14546; A61M 5/1456; A61M 5/16827; A61M 5/007
See application file for complete search history.

(56) References Cited

U.S. PATENT DOCUMENTS 6,035,328 A  3/2000 Soukal
6,397,098 B1* 5/2002 Uber et al. ................ 600/431
(Continued)

FOREIGN PATENT DOCUMENTS

JP   H10 14900 A   1/1998
JP   2001-149354 A   6/2001
(Continued)

OTHER PUBLICATIONS

International Search Report for PCT/JP2007/065269, dated Nov. 6, 2007.
(Continued)

*Primary Examiner* — Long V. Le
*Assistant Examiner* — Colin T Sakamoto
(74) *Attorney, Agent, or Firm* — Knobbe, Martens, Olson & Bear LLP (57) ABSTRACT

An X-ray CT system (1000) includes a CT scanner (300) which obtains diagnostic images of a patient, a chemical liquid injector (100) which injects a chemical liquid into a patient whose images are obtained, an operation device (400), I/Fs (320, 421) for transmitting and receiving data between the CT scanner (300) and the operation device (400) and I/Fs (120, 420) for transmitting and receiving data between the chemical liquid injector (100) and the operation device (400). The operation device includes an input section used to set an injection condition for the chemical liquid by the chemical liquid injector (100) and an imaging condition by the CT scanner (300), a control section for controlling operation of the chemical liquid injector (100) and operation of the CT scanner (300) in accordance with the setting and a display section (450) for displaying information relating to the setting of the injection condition and the imaging condition and an obtained image.

4 Claims, 4 Drawing Sheets

(51) Int. Cl.
  *H05G 1/30* (2006.01)
  *A61M 5/00* (2006.01)
  *A61M 5/145* (2006.01)
  *A61M 5/168* (2006.01)

(52) U.S. Cl.
  CPC ....... *A61M 5/1456* (2013.01); *A61M 5/14546* (2013.01); *A61M 5/16827* (2013.01); *A61M 2205/502* (2013.01)

(56) References Cited

U.S. PATENT DOCUMENTS

| | | | | |
|---|---|---|---|---|
| 6,647,283 | B2* | 11/2003 | Klotz | 600/425 |
| 7,128,729 | B2* | 10/2006 | Duchon et al. | 604/154 |
| 7,974,682 | B2* | 7/2011 | Gonzalez Molezzi et al. | 600/432 |
| 2004/0172303 | A1* | 9/2004 | Declerck et al. | 705/2 |
| 2004/0199076 | A1* | 10/2004 | Nemoto | 600/432 |
| 2005/0203389 | A1* | 9/2005 | Williams | 600/431 |
| 2007/0255135 | A1* | 11/2007 | Kalafut et al. | 600/431 |
| 2009/0177050 | A1* | 7/2009 | Griffiths et al. | 600/301 |
| 2009/0214094 | A1* | 8/2009 | Williams et al. | 382/131 |
| 2010/0160776 | A1* | 6/2010 | Goto et al. | 600/431 |
| 2010/0174181 | A1* | 7/2010 | Nemoto | 600/431 |
| 2010/0217121 | A1* | 8/2010 | Nemoto | 600/432 |
| 2011/0178359 | A1* | 7/2011 | Hirschman et al. | 600/4 |

FOREIGN PATENT DOCUMENTS

| | | |
|---|---|---|
| JP | 2003 47608 A1 | 2/2003 |
| JP | 2004-298610 | 10/2004 |
| JP | 2005-198808 | 7/2005 |
| JP | 2007-143880 | 6/2007 |
| JP | 2007-181707 | 7/2007 |
| WO | WO 2005/007220 | 1/2005 |
| WO | WO 2005/076810 | 8/2005 |

OTHER PUBLICATIONS

English translation of Japanese Office Action dated Nov. 6, 2012, Japanese Application No. 2008-528800.

English translation of Japanese Office Action dated Aug. 7, 2012, Japanese Application No. 2008-528800.

English translation of Japanese Office Action dated Apr. 25, 2012, JP Application No. 2008-528800.

English translation of Japanese Office Action dated Apr. 22, 2014, JP Application No. JP 2008-528800.

Office Action issued in Japanese Patent Application No. 2014-127110, dated Mar. 24, 2015.

\* cited by examiner

X-RAY CT SYSTEM, CHEMICAL LIQUID INJECTOR, AND CT SCANNER

This application is the U.S. National Phase under 35 U.S.C. § 371 of International Application PCT/JP2007/065269, filed Aug. 3, 2007, which claims priority to Japanese Patent Application No. 2006-214697, filed Aug. 7, 2006. The International Application was published under PCT Article 21(2) in a language other than English.

TECHNICAL FIELD

The present invention relates to an X-ray CT system for obtaining diagnostic images of a patient, and more particularly, to an X-ray CT system which includes a chemical liquid injector for injecting a chemical liquid such as a contrast medium into a patient whose diagnostic images are taken, and to the chemical liquid injector and a CT scanner thereof.

BACKGROUND ART

An X-ray CT (Computed Tomography) apparatus is a representative imaging diagnostic apparatus for medical purposes. When the X-ray CT apparatus is used, a chemical liquid such as a contrast medium and physiological saline is often injected into a patient in order to provide favorable diagnostic images. Chemical liquid injectors for automatically injecting the chemical liquid have been put into practical use.

For obtaining favorable images with the X-ray CT apparatus, it is important to start imaging after the lapse of a predetermined time period from the injection of the chemical liquid by the chemical liquid injector. Thus, if a single operator performs operations for injecting the chemical liquid and operations for obtaining diagnostic images, the operator should perform those complicated operations.

To address this, Patent Document 1 has disclosed that an X-ray CT apparatus and a chemical liquid injector communicate data with each other to associate the operation of chemical liquid injection by the chemical liquid injector with the operation of imaging by the X-ray CT apparatus. For example, obtaining of diagnostic images is started after the lapse of a predetermined time period from the start of chemical liquid injection in Patent Document 1.

In the invention disclosed in Patent Document 1, diagnostic images can be automatically obtained by the X-ray CT apparatus only if the operation of the chemical liquid injector is started, for example. This can reduce the workload for the operator.

In actual operations, however, the operator needs to enter and set data representing injection conditions for a patient such as his ID, weight, gender, height, body region to be imaged, and injection time period into the chemical liquid injector prior to injection of a chemical liquid. In addition, it is necessary to enter and set data representing imaging conditions for the patient such as his ID, body region to be imaged, imaging time period, and X-ray exposure conditions into the X-ray CT apparatus prior to obtaining of diagnostic images.

The setting of the injection conditions and the setting of the imaging conditions are separately performed in the chemical liquid injector and the X-ray CT apparatus, respectively. The injection conditions and imaging conditions to be set have some of the items in common. Even for the common items, the operator should enter them into both of the chemical liquid injector and the X-ray CT apparatus. For example, if some of the injection conditions are changed and the changed items are common to the injection conditions and the imaging conditions, the imaging conditions need to be changed in the X-ray CT apparatus. However, the operator may forget to change the imaging conditions.

Both of the chemical liquid injector and the X-ray CT apparatus have input means for inputting the injection conditions and the imaging conditions and display means for displaying the input details and the operation situations of them. Both of these input means and display means of the chemical liquid injector and the X-ray CT apparatus are often placed in an operation room. Thus, the input means and the display means of the chemical liquid injector and the input means and the display means of the X-ray CT apparatus are located in the operation room, which clutters the operation room.

Patent Document 1: Japanese Patent Laid-Open No. 2004-298610

DISCLOSURE OF THE INVENTION

It is an object of the present invention to provide an X-ray CT system which has a simplified configuration including an X-ray CT apparatus and a chemical liquid injector to achieve higher efficiency of operation and saving of space.

To accomplish the abovementioned object, an X-ray CT system according to the present invention includes a CT imaging section which obtains diagnostic images of a patient, a chemical liquid injection section which injects a chemical liquid into a patient whose images are obtained, and an operation section. In the operation section, conditions of injection of the chemical liquid in the chemical liquid injection section and imaging conditions in the CT imaging section are set. The operation section controls the operations of the chemical liquid injection section and the CT imaging section and displays information relating to the setting of the injection condition and the imaging condition and an obtained image. The X-ray CT system according to the present invention also includes an interface section for transmitting and receiving data between the CT imaging section and the operation section, and an interface section for transmitting and receiving data between the chemical liquid injection section and the operation section.

A chemical liquid injector according to the present invention is used as the chemical liquid injection section of the abovementioned X-ray CT system of the present invention and includes an interface section for transmitting and receiving data between the operation section of the X-ray CT system and the chemical liquid injector.

A CT scanner according to the present invention is used as the CT imaging section of the abovementioned X-ray CT system of the present invention and includes an interface section for transmitting and receiving data between the operation section of the X-ray CT system and the CT scanner.

In the present invention configured as described above, the system includes the common operation section for setting the injection conditions of the chemical liquid and the imaging conditions of images and for providing images to be shown to an operator. This allows the data to be shared by the chemical liquid injection section and the CT imaging section.

According to the present invention, since the operation section is common to the CT imaging section and the chemical liquid injection section, the X-ray CT system can have a simplified configuration and thus can be placed in saved space. The common operation section also enables the data sharing, so that the data input can be simply performed in setting the injection conditions of the chemical liquid and the imaging conditions of images, thereby achieving efficient operation.

DESCRIPTION OF REFERENCE NUMERALS

100 CHEMICAL LIQUID INJECTOR
130 PISTON DRIVING MECHANISM
120, 320, 420, 421 INTERFACE SECTIONS
300 CT SCANNER
400 OPERATION DEVICE
410 OVERALL CONTROL SECTION
411 INJECTOR CONTROL SECTION
412 SCANNER CONTROL SECTION
430 STORAGE SECTION
440 INPUT SECTION
450 DISPLAY SECTION

BEST MODE FOR CARRYING OUT THE INVENTION

Figure 1:
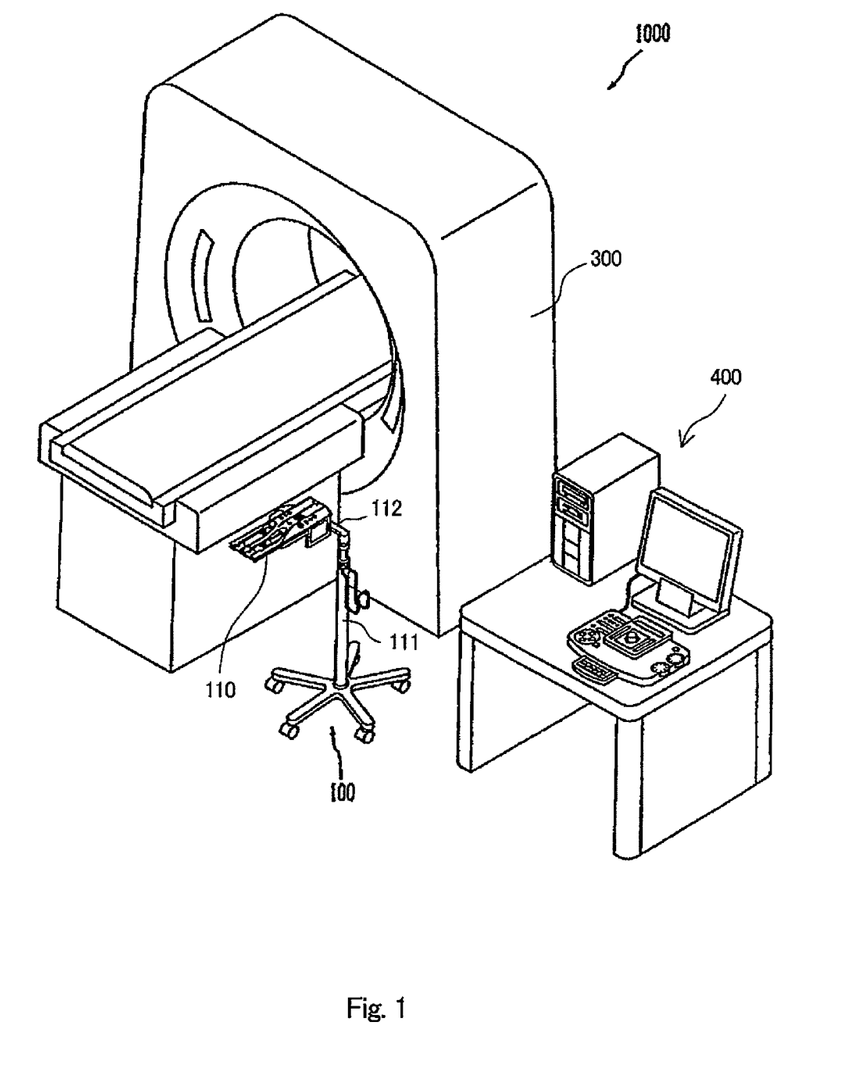
FIG. 1 is a perspective view showing the outer appearance of an X-ray CT system according to an embodiment of the present invention.

Referring to FIG. 1, CT system 1000 according to an embodiment of the present invention is shown which includes chemical liquid injector 100 serving as a chemical liquid injection section, CT scanner 300 serving as a CT imaging section, and operation device 400 for them. Chemical liquid injector 100 and CT scanner 300 are wirelessly connected or wire-connected to operation device 400 such that the former can communicate data with the latter. While FIG. 1 shows all of chemical liquid injector 100, CT scanner 300, and operation device 400 placed in the same room, operation device 400 is located in a room different from the room where chemical liquid injector 100 and CT scanner 300 are placed when CT system 1000 is actually used to obtain diagnostic images of a patient.

CT scanner 300 is an apparatus which obtains diagnostic images of the body of a patient by irradiating the patient with X-rays and back-projecting the body of the patient based on the X-rays passed through the patient. CT scanner 300 includes, as its main components, a bed, an X-ray source for irradiating a patient lying on the bed with X-rays, and an X-ray detector placed opposite to the X-ray source to detect the X-rays passed through the patient.

Chemical liquid injector 100 includes injection head 110 attached to the top of arm 112 coupled to stand 111, for example. Injection head 110 is connected to operation device 400.

Figure 2:
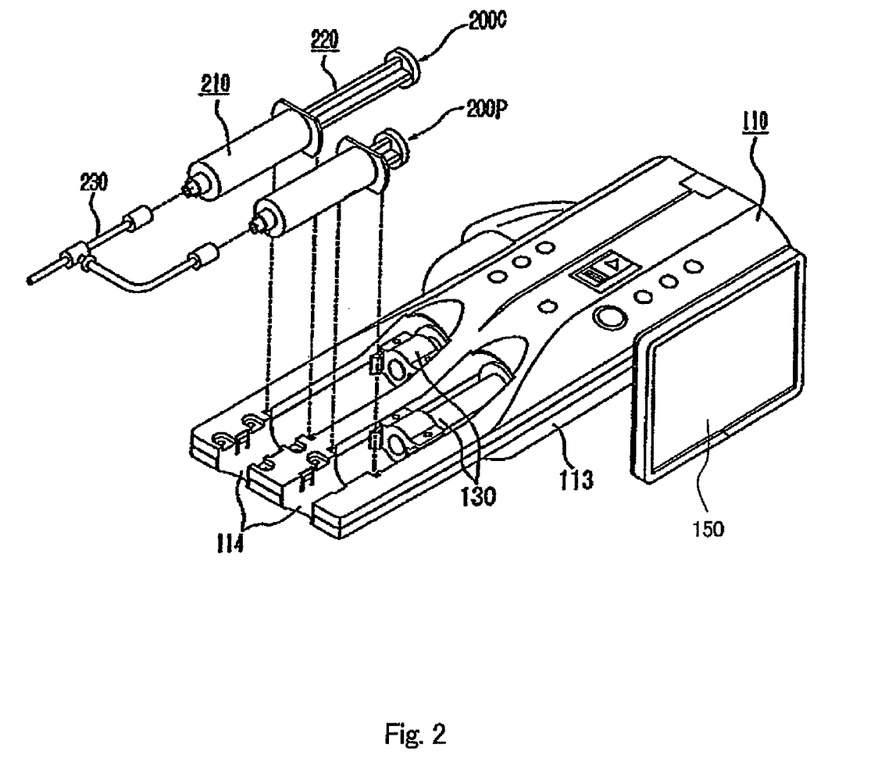
FIG. 2 is a perspective view showing an injection head shown in FIG. 1 together with syringes to be mounted thereon.

As shown in FIG. 2, injection head 110 has head body 113. Head body 113 has two concave portions 114 as syringe holding portions formed in its upper surface. Two syringes 200C and 200P are mounted on these concave portions 114 respectively. For example, one syringe 200C is filled with a contrast medium for CT as a chemical liquid, while the other syringe 200P is filled with physiological saline as a chemical liquid. Each of syringes 200C and 200P has cylinder 210 and piston 220. The ends of two syringes 200C and 200P mounted on head body 113 are connected with connection tube 230. A catheter (not shown) which is to be inserted into a blood vessel of the patient is connected to the end of connection tube 230.

Injection head 110 also has two piston driving mechanisms 130 which are driven independently. Piston driving mechanisms 130 can be used to push pistons 220 of syringes 200C and 200P mounted in concave portions 114 into cylinders 210 to inject the contrast medium and the physiological saline contained in syringes 200C and 200P into the patient separately or simultaneously.

Injection head 110 also has operation button 140 serving as a sub-operation section and liquid crystal display 150 serving as a sub-display section.

Operation device 400 is manipulated by an operator to enter and set data representing conditions of chemical liquid injection by chemical liquid injector 100 and conditions of diagnostic image obtaining by CT scanner 300. Operation device 400 controls the operation of chemical liquid injector 100 and the operation of CT scanner 300 in accordance with the settings. Operation device 400 can display, as required, a set information window for use in setting the injection conditions, a set information window for use in setting the imaging conditions, a window showing operation information of chemical liquid injector 100 in the chemical liquid injection, and a window showing operation information of CT scanner 300 in the diagnostic image obtaining, and an image obtained by CT scanner 300.

Figure 3:
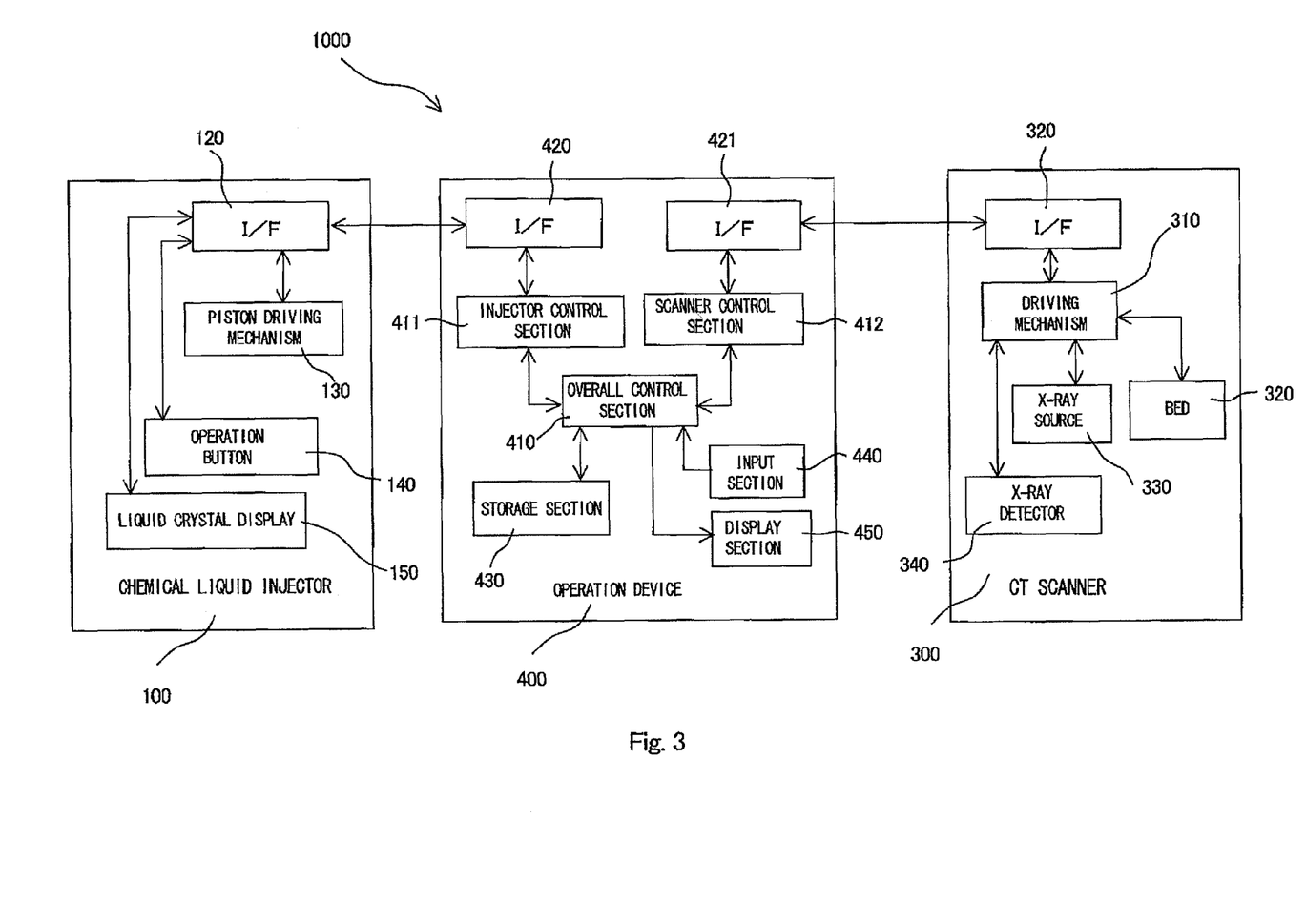
FIG. 3 is a block diagram showing the X-ray CT system shown in FIG. 1.

FIG. 3 shows a block diagram showing X-ray CT system 1000 of the embodiment.

From the functional viewpoint of X-ray CT system 1000 of the embodiment, operation device 400 includes a control section for controlling the overall operation of X-ray CT system 1000, input section 440, display section 450, and storage section 430.

Input section 440 is a device which is used by an operator to enter data for obtaining the injection conditions of the chemical liquid and the imaging conditions of diagnostic images. A device for data entry such as a keyboard can be used as input section 440. Display section 450 is a device which realizes the display function in operation device 400, as described above. For example, a CRT display or a liquid crystal display can be used as display section 450. While input section 440 and display section 450 can be formed of separate units, it is possible that a touch panel can be used and the single unit can realize at least some of the functions of input section 440 and at least some of the functions of display section 450, for example.

The control section includes injector control section 411 for controlling the operation of chemical liquid injector 100, scanner control section 412 for controlling the operation of CT scanner 300, and overall control section 410 for controlling the overall operation of X-ray CT system 1000 including them. Especially, overall control section 410 determines the injection conditions of the chemical liquid and the imaging conditions of diagnostic images based on the data input through input section 440 and transmits the injection conditions and the imaging conditions to injector control section 411 and scanner control section 412, respectively. Overall control section 410 also controls the operation timing of chemical liquid injector 100 and CT scanner 300. For example, overall control section 410 causes CT scanner 300 to operate after the lapse of a predetermined time period from the start of injection operation by chemical liquid injector 100.

Injector control section 411, scanner control section 412, and overall control section 410 may be formed as separate units or may be formed as a single unit.

Storage section 430 saves (stores) various types of data input through input section 440, and the injection conditions and the imaging conditions determined on the basis of the input data and the like.

Operation device 400 also includes interface section (I/F) 420 for transmitting and receiving data to and from chemical liquid injector 100 and interface section (I/F) 421 for transmitting and receiving data to and from CT scanner 300. Chemical liquid injector 100 and CT scanner 300 include interface sections (I/F) 120 and 320, respectively, for transmitting and receiving data to and from the operation device.

An instruction from injector control section 411 is transmitted to chemical liquid injector 100 via I/F 420 and I/F 120 to cause piston driving mechanism 130 and liquid crystal display 150 of chemical liquid injector 100 to operate. On the contrary, operation information of piston driving mechanism 130 of chemical liquid injector 100 and input information from operation button 140 are transmitted to operation device 400 via I/F 120 and I/F 420.

In addition to bed 320, X-ray source 330, and X-ray detector 340 described above, CT scanner 300 also has driving mechanism 310 for driving them. An instruction from scanner control section 412 is transmitted to driving mechanism 310 of CT scanner 300 via I/F 421 and I/F 320 to cause the units such as bed 320 and X-ray source 330 to operate. On the contrary, operation information of each unit of CT scanner 300 is transmitted to operation device 400 via I/F 320 and I/F 421.

Next, an example of the operation of X-ray CT system 1000 described above will be described.

First, X-ray CT system 1000 performs injection of the chemical liquid into a patient. Prior to the injection of the chemical liquid, an operator enters the ID number of the patient, data necessary for determining the injection conditions of the chemical liquid in chemical liquid injector 100, and data necessary for determining the imaging conditions of images in CT scanner 300 through the input section of operation device 400.

At the time of entering data, overall control section 410 displays the window for setting the injection conditions and the window for setting the imaging conditions in display section 450 such that the windows can be switched. The switching of the windows can be performed automatically by overall control section 410 or can be performed arbitrarily with the manipulation of the operator. The switching of the windows can be performed such that only one of the window for setting the injection conditions and the window for setting the imaging conditions is displayed in display section 450 or both of the windows are displayed simultaneously. When both of the windows are displayed simultaneously, one of the window for setting the injection conditions and the window for setting the imaging conditions can be displayed in a larger size and the other can be displayed in a smaller size depending on whether the injection conditions or the imaging conditions are to be input, or one of the windows is overlaid on part of the other window.

Figure 4:
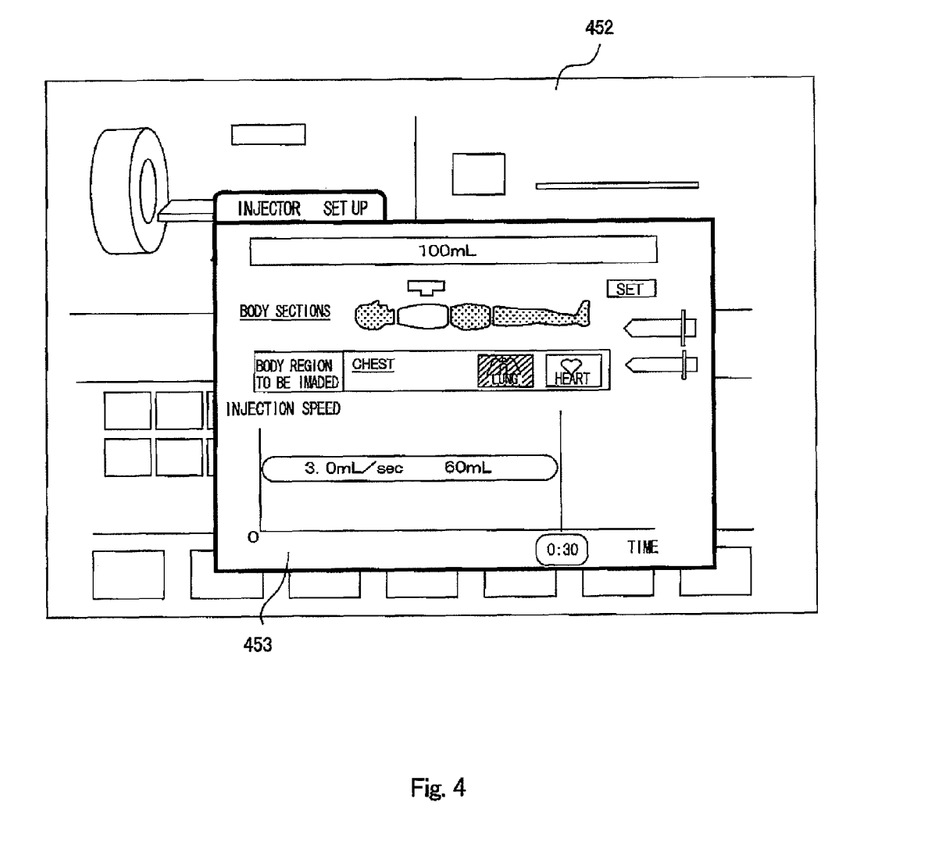
FIG. 4 is a diagram showing an example of a display screen in a display section when injection conditions are set.

FIG. 4 illustrates an example of the windows shown in display section 450 when the injection conditions are set. In the example shown in FIG. 4, window 452 for setting the imaging conditions is displayed over the whole screen, and window 453 for setting the injection conditions is overlaid in a smaller size than the size of window 452 for setting the imaging conditions. Window 453 for setting the injection conditions displays the capacity of the syringe, the body region of the patient to be imaged, a graph representing the relationship between the injection speed and injection time period of the chemical liquid, the injection quantity of the chemical liquid and the like.

Window 453 for setting the injection conditions has a tab labeled as "injector set up," for example. After the setting of the injection conditions, the tab can be manipulated by the operator to display only window 452 for setting the imaging conditions. Window 452 for setting the imaging conditions has a tab or an icon for displaying window 453 for setting the injection conditions. The tab or icon can be manipulated to display the window for setting the injection conditions again. The switching of the windows may also be performed by pressing a key provided for input section 440.

The data entered in determining the injection conditions includes, for example, the ID of the patient, the body characteristics of the patient (such as his weight, height, gender, and age), the characteristics of the chemical liquid (such as the type of the chemical liquid and the concentrations of the ingredients), and the body region to be imaged. Overall control section 410 determines the injection conditions such as the injection quantity, the injection speed, the injection time period, and the injection pressure of the chemical liquid based on the input data. The injection conditions can be determined by performing arithmetic processing in which the input data is substituted into a predetermined expression, by consulting a database stored in storage section 430, for example, or by a combination thereof.

The data entered in determining the imaging conditions includes, for example, the ID of the patient, the body characteristics of the patient, the type of the chemical liquid, the body region to be imaged, a scan mode, a scan time, and a scan speed. Overall control section 410 determines the imaging conditions such as the movement amount of the bed, the movement amount and speed of the X-ray source, and the exposure conditions of X-rays based on the input data. The determination of the imaging conditions can be performed by arithmetic processing, consultation of the database, or a combination of them, similarly to the determination of the injection conditions.

In determining the injection conditions and the imaging conditions, the operator may directly enter and set, through input section 440, at least some of the conditions determined by arithmetic processing or consultation of the database.

The data entered in determining the injection conditions and the data entered in determining the imaging conditions have some items in common. Thus, in the embodiment, the entered data is stored in storage section 430. In the injection conditions or the imaging conditions that are input later, the data items thereof common to both of them are reflected from the corresponding data items entered earlier to omit redundant entry of those data items. In display section 450, when there are input data items identical to input data items of the conditions entered earlier, the previously input data is displayed, and the fact that they are previously input items is indicated to the operator.

If the ID of the patient and the associated body characteristics of the patient are stored in a database in storage section 430, the ID of the patient can be entered by the operator to display the body characteristics of the patient associated with the ID on a data input window of display section 450 to omit entry of the body characteristics when data is entered for determining the injection conditions and the imaging conditions. In addition, if the imaging history for each patient is stored in a database in storage section 430, the ID of the patient can be entered by the operator to display the data items input in the previous imaging on the data input window when data is entered for determining the injection conditions and the imaging conditions. The operator can change, as required, the body characteristics of the patient displayed on the data input window and the data items entered in the previous imaging.

While the data is entered through input section 440 as described above, the operator who enters the data or another operator mounts syringes 200C and 200P on injection head 110, connects syringes 200C and 200P with connection tube 230, and inserts the catheter provided for the end of connection tube 230 into a blood vessel of the patient.

At least some of the injection conditions determined in operation device 400 and the data entered through input section 440 are displayed on Liquid crystal display 150 of chemical liquid injector 100. The injection conditions and the data shown on liquid crystal display 150 can be changed with operation button 140. In other words, the injection conditions or the data can be changed on the side of chemical liquid injector 100.

After the abovementioned preparations are completed, the operator starts the operation of X-ray CT system 1000 through the manipulation of operation device 400. For starting the operation of X-ray CT system 1000, input section 440 of operation device 400 can have a start button which is mechanically manipulated, or display section 450 can show an icon for start which is manipulated by software.

In any case, when the manipulation for starting operation is performed, overall control section 410 issues an instruction for starting the operation of chemical liquid injector 100 to injector control section 411. Upon issue of the operation start instruction, injector control section 411 controls the operation of chemical liquid injector 100 in accordance with the determined injection conditions to inject the chemical liquid into the patient.

After the lapse of a predetermined time period from the start of the chemical liquid injection, overall control section 410 issues an instruction for starting the operation of CT scanner 300 to scanner control section 412. Upon issue of the operation start instruction, CT scanner 300 controls the operation of CT scanner 300 in accordance with the determined imaging conditions to obtain diagnostic images of the patient.

During the injection operation of the chemical liquid and the obtaining operation of diagnostic images, overall control section 410 displays graphics representing the operation situations of chemical liquid injector 100 and CT scanner 300 with animation or the like in display section 450. When both of chemical liquid injector 100 and CT scanner 300 operate simultaneously, the operation graphics to be shown in display section 450 may be previously set in overall control section 410 or may be set or switched arbitrarily by the operator.

After the imaging operation by CT scanner 400 is completed, overall control section 410 reconfigures images based on the data obtained in the imaging operation and displays them as diagnostic images of the patient in display section 450.

As described above, according to the embodiment, the single operation device 400 can be used to perform both of the data entry for setting the injection conditions of the chemical liquid in chemical liquid injector 100 and the data entry for setting the imaging conditions of images in CT scanner 300.

Thus, chemical liquid injector 100 and CT scanner 300 can share input section 440 for inputting the data and the like and display section 450 for outputting the information, thereby achieving a simplified configuration of overall X-ray CT system 1000 including chemical liquid injector 100 and CT scanner 300. As a result, only one input section 440 and only one display section 450 are sufficient, so that the space is saved to allow operation device 400 to be placed in a smaller space than in the conventional example.

Since operation device 400 is common to chemical liquid injector 100 and CT scanner 300, the entry of redundant data items can be omitted when the data is input for setting the injection conditions of the chemical liquid and the data is input for setting the imaging conditions of images. Consequently, the number of input data items can be reduced. In addition, for example when the data is modified or changed, the modification of data is not needed on both of chemical liquid injector 100 and CT scanner 300 as in the conventional example, and only by modifying the data on the input window for setting one of the injection conditions and the imaging conditions, the modified data can be reflected in determining the other conditions. It is thus possible to enter the data for setting the injection conditions and the imaging conditions efficiently and to reduce errors in the data input.

The invention claimed is:

1. An X-ray CT system comprising:
   a CT imaging section configured to obtain a diagnostic image of a patient;
   a chemical liquid injection section configured to inject a chemical liquid into the patient whose image is to be obtained, the chemical liquid injection section including a sub-display unit configured to display injection conditions;
   an operation section for the CT imaging section and the chemical liquid injection section;
   an interface section for transmitting and receiving data between the CT imaging section and the operation section; and
   an interface section for transmitting and receiving data between the chemical liquid injection section and the operation section;
   wherein the operation section comprises:
      a display unit configured to display a window showing information about the CT imaging section including input data items for setting an imaging condition, and a window showing information about the chemical liquid injection section including input data items for setting an injection condition;
      an input device used for entering data into the input data items for setting an imaging condition by the CT imaging section and for entering data into the input data items for setting an injection condition for the chemical liquid by the chemical liquid injection section;
   a scanner control section for controlling operation of the CT imaging section;
   an injector control section for controlling operation of the chemical liquid injection section;
   an overall control section configured to:
      display a window for setting a first condition on the display unit, the first condition is the imaging condition or the injection condition where a second condition is the other condition;
      receive data from the input device for the first condition;
      display a window for setting the second condition on the display unit;

when there is one or more identical input data items for the second condition that are identical to input data items for the first condition,     display a data of the identical input data item that received data for the first condition in the window for setting the second condition, and     receive data input through the input device for input data items of the second condition that are different from the data items for the first condition; and determine the imaging condition and the injection condition based, at least in part, on the one or more identical input data items and the data input through the input device for the first condition and the second condition, and transmit the imaging condition and the injection condition to the scanner control section and the injector control section, respectively; and a storage section configured to store data entered through the input device;

wherein the scanner control section is configured to control operation of the CT imaging section in accordance with the determined imaging condition; and wherein the injector control section is configured to control operation of chemical liquid injection section in accordance with the determined injection condition.

2. The X-ray CT system according to claim 1, wherein the display unit is controlled by the overall control section such that a window which displays information relating to the chemical liquid injection section and a window which displays information relating to the CT imaging section are switched.

3. The X-ray CT system according to claim 1, wherein the overall control section issues an instruction for starting the operation of the CT imaging section to the scanner control section.

4. An operation controller for a CT system, the CT system configured to inject a chemical liquid into a patient whose image is to be obtained, and to obtain the image, the operation controller comprising:

a display unit configured to display a window showing information including input data items for setting an imaging condition, and a window showing information including input data items for setting an injection condition;

an input device used for entering data into the input data items for setting an imaging condition and for entering data into the input data items for setting an injection condition;

a scanner control section for controlling an imaging operation, the imaging operation configured to obtain the image of the patient, an injector control section for controlling operation of a chemical liquid injector for injecting the chemical liquid into the patient, an overall control section configured to:

display a window for setting a first condition, the first condition is the imaging condition or the injection condition where a second condition is the other condition, on the display unit;

receive data from the input device for the input data items of the first condition;

display a window for setting the second condition on the display unit;

when there is one or more identical input data items for the second condition that are identical to input data items for the first condition,         display a data of the identical input data item that received data for the first condition in the window for setting the second condition, and         receive data input through the input device for input data items of the second condition that are different from the data items for the first condition; and     determine the imaging condition and the injection condition based, at least in part, on the one or more identical input data items and the data input through the input device for the first condition and the second condition, and transmit the imaging condition and the injection condition to the scanner control section and the injector control section, respectively; and a storage section configured to store data entered through the input device;

wherein the scanner control section is configured to control the imaging operation in accordance with the determined imaging condition; and wherein the injector control section is configured to control operation of the chemical liquid injector in accordance with the determined injection condition.

\* \* \* \* \*

UNITED STATES PATENT AND TRADEMARK OFFICE
CERTIFICATE OF CORRECTION

PATENT NO. : 9,918,687 B2  
APPLICATION NO. : 12/376955  
DATED : March 20, 2018  
INVENTOR(S) : Shigeru Nemoto

Page 1 of 1

It is certified that error appears in the above-identified patent and that said Letters Patent is hereby corrected as shown below:

In the Specification

In Column 4, at Line 11 (Approx.), Change "2000" to --200C--.

Signed and Sealed this
Nineteenth Day of March, 2019

Andrei Iancu
*Director of the United States Patent and Trademark Office*